(12) United States Patent
Dickerson

(10) Patent No.: US 7,914,488 B2
(45) Date of Patent: Mar. 29, 2011

(54) SAFETY NEEDLE INTRODUCER AND UNIVERSAL NEEDLE PROTECTOR FOR VASCULAR ACCESS DEVICES

(75) Inventor: Charles W. Dickerson, Tustin, CA (US)

(73) Assignee: C. Dickerson Co., Henderson, NV (US)

( * ) Notice: Subject to any disclaimer, the term of this patent is extended or adjusted under 35 U.S.C. 154(b) by 0 days.

(21) Appl. No.: 10/154,590

(22) Filed: May 22, 2002

(65) Prior Publication Data
US 2003/0220617 A1 Nov. 27, 2003

(51) Int. Cl.
*A61M 5/00* (2006.01)
(52) U.S. Cl. ........................................... 604/110
(58) Field of Classification Search .............. 604/263, 604/192, 162, 198, 110, 164.01, 164.08, 604/165.01, 165.02, 167.01, 167.02, 171, 604/158, 93.01
See application file for complete search history.

(56) References Cited

U.S. PATENT DOCUMENTS

| | | | |
|---|---|---|---|
| 4,725,267 A | | 2/1988 | Vaillancourt |
| 4,762,516 A | * | 8/1988 | Luther et al. ............. 604/164.08 |
| 4,790,828 A | | 12/1988 | Dombrowski et al. |
| 4,826,491 A | * | 5/1989 | Schramm ....................... 604/198 |
| 4,944,725 A | * | 7/1990 | McDonald ............... 604/164.08 |
| 4,950,252 A | | 8/1990 | Luther et al. |
| 4,978,344 A | | 12/1990 | Dombrowski et al. |
| 4,994,041 A | | 2/1991 | Dombrowski et al. |
| 4,994,046 A | * | 2/1991 | Wesson et al. ................. 604/198 |
| 5,026,356 A | * | 6/1991 | Smith ............................ 604/192 |
| 5,163,916 A | * | 11/1992 | Sunderland .................... 604/198 |
| 5,215,528 A | | 6/1993 | Purdy et al. |
| 5,273,540 A | | 12/1993 | Luther et al. |
| 5,456,668 A | * | 10/1995 | Ogle, II ......................... 604/110 |
| 5,533,988 A | | 7/1996 | Dickerson et al. |
| 5,562,624 A | | 10/1996 | Righi et al. |
| 5,569,202 A | | 10/1996 | Kovalic et al. |
| 5,662,610 A | | 9/1997 | Sircom |
| 5,683,370 A | | 11/1997 | Luther et al. |
| 5,688,249 A | * | 11/1997 | Chang et al. .................. 604/198 |
| 5,700,249 A | | 12/1997 | Jenkins |
| 5,817,060 A | | 10/1998 | Overton et al. |
| 5,873,864 A | | 2/1999 | Luther et al. |
| 5,879,337 A | | 3/1999 | Kuracina et al. |
| 6,001,080 A | | 12/1999 | Kuracina et al. |
| 6,106,499 A | | 8/2000 | Overton et al. |
| 6,156,010 A | | 12/2000 | Kuracina et al. |
| 6,261,264 B1 | | 7/2001 | Tamaro |

* cited by examiner

*Primary Examiner* — Nicholas D Lucchesi
*Assistant Examiner* — Laura A Bouchelle
(74) *Attorney, Agent, or Firm* — Orrick, Herrington & Sutcliffe, LLP

(57) ABSTRACT

A needle point protective device for hypodermic and intravenous needles, catheter introducers, and similar devices protects users from injury and infection. The needle point protective device includes a needle point guard that is slidably mounted within the needle handle. In use, the needle point guard is integral with a cannula guide that is engaged with the needle cannula with enough force to cause the needle cannula to be subject to spring tension when the needle point is retracted proximal to the needle point guard, the needle point springs downward and behind the needle point guard. In one embodiment, the needle point guard is held in position manually as the needle is retracted. In another embodiment, the needle point guard is held in place automatically as the needle is retracted.

11 Claims, 8 Drawing Sheets

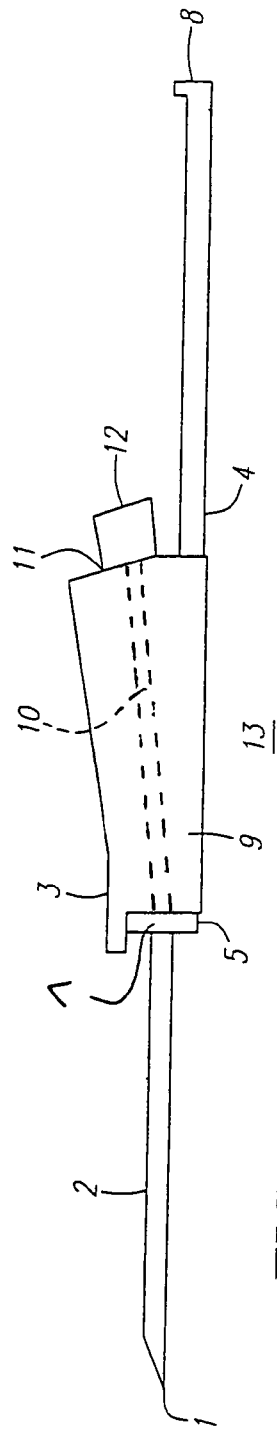
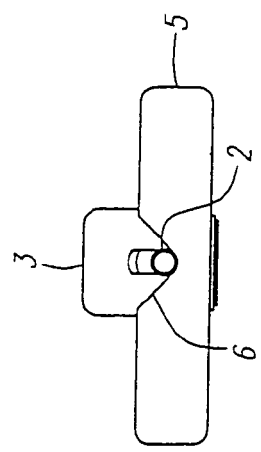
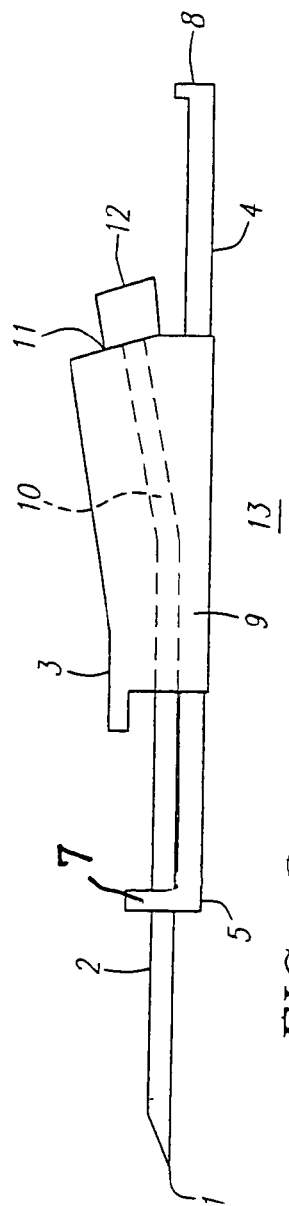

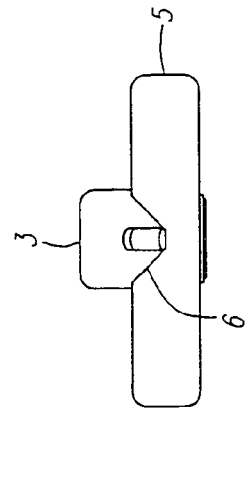
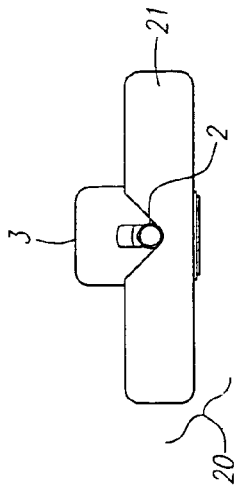
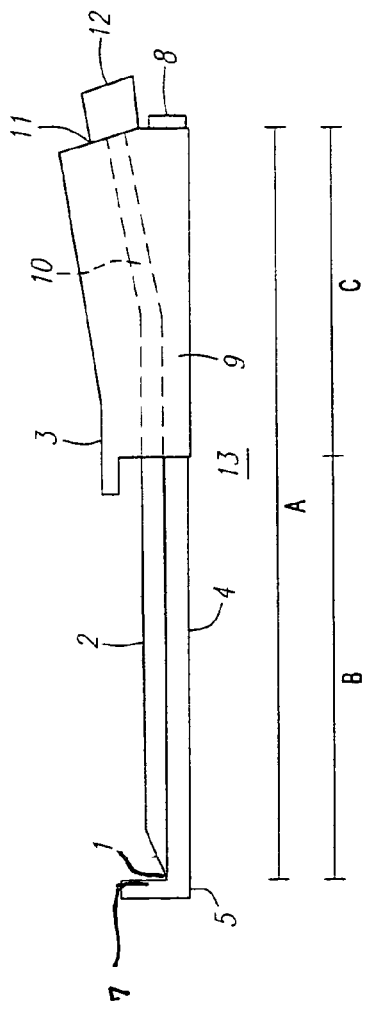
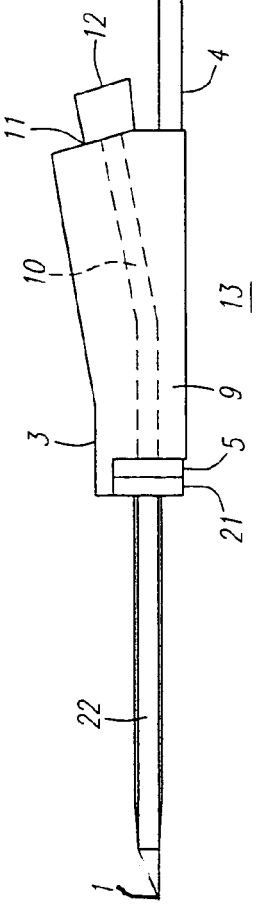

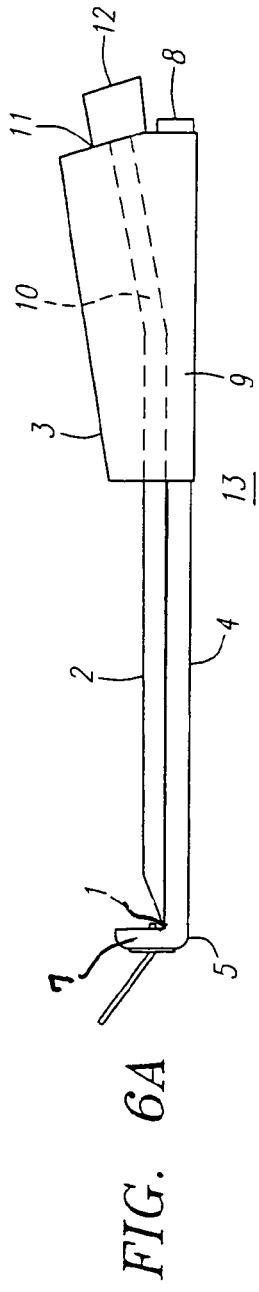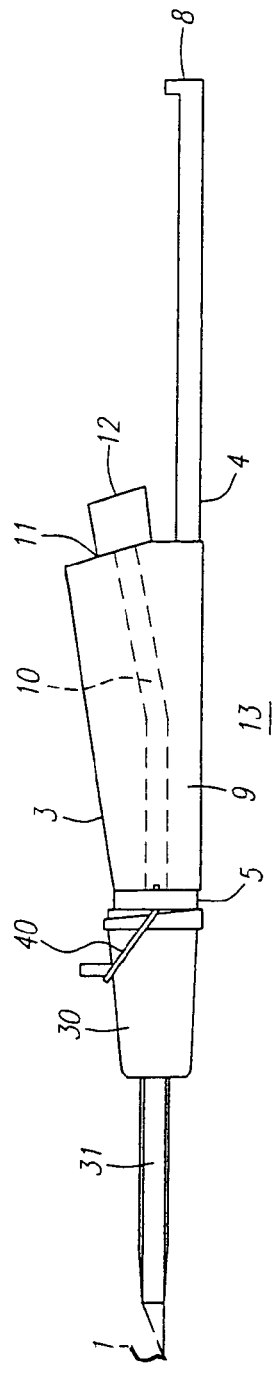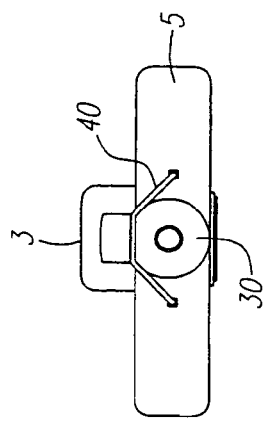

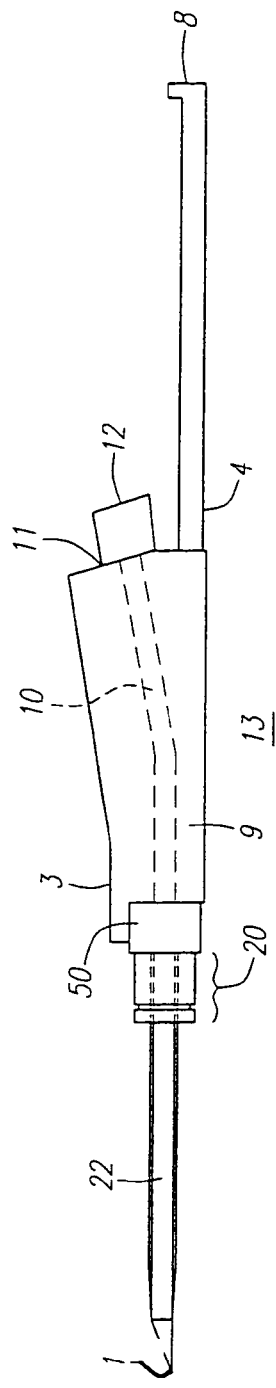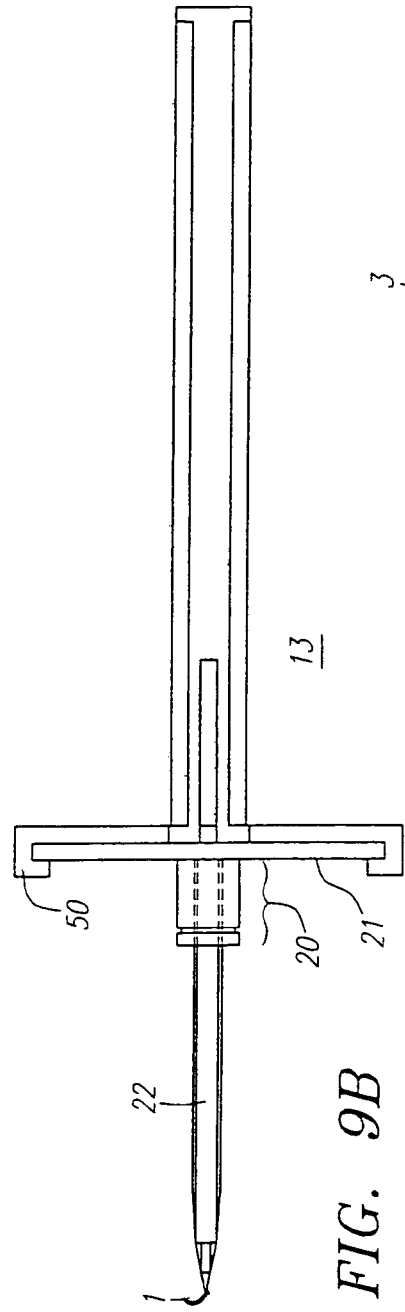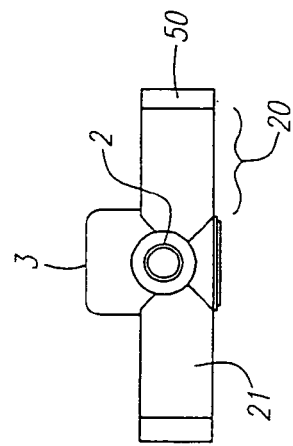
FIG. 9A
FIG. 9B
FIG. 9C

SAFETY NEEDLE INTRODUCER AND UNIVERSAL NEEDLE PROTECTOR FOR VASCULAR ACCESS DEVICES

FIELD OF THE INVENTION

The present invention relates to needle point protectors and assemblies of devices including needle point guards that are used for safety purposes with hypodermic and intravenous needles.

BACKGROUND OF THE INVENTION

The dangers of infection from accidental contact with the sharpened points of used hypodermic needles are well documented. The proliferation of Human immunodeficiency Virus (HIV), combined with the increasing incidence of other bloodborne pathogens such as Hepatitis B Virus and Hepatitis C Virus, present healthcare workers with a serious occupational hazard. More than twenty known bloodborne pathogens, which are transmitted via blood and bodily fluids, are present inside the bore of a used needle and can be transmitted to another person after the needle has been used with an infected patent. The presence of any of these pathogens in infected patients poses a risk of transmitting a deadly disease to healthcare workers when virtually any procedure is performed in which a needle penetrates the patient's skin.

Infectious diseases have become the third leading cause of death; the prevalence of those diseases creates a growing need for needle protection devices that provide a margin of safety to the healthcare worker. Healthcare workers routinely perform several types of invasive hypodermic and intravenous procedures, such as injecting medicine, collecting blood, establish intravenous (i.v.) fluid administration, and inserting indwelling intravenous catheters. During or after these procedures, nurses and other healthcare personnel are routinely injured by the exposed sharpened end of the needle after use on a patient. Although the danger exists at several points in time, an injury by a needle point, sometimes called a "needle stick" injury, is most likely to occur between the moment that a needle is withdrawn from a patient and the time at which the contaminated needle is safely discarded.

The jobs of approximately 5.6 million workers in the United States place them at risk for accidental needle stick injuries. Medical literature cites approximately one million reported needle stick accidents that occur in the United States each year, with an additional 700,000 believed to be unreported. Prior to high rates of HIV and serum hepatitis, a needle stick injury was considered a routine nuisance that was accepted as part of providing patient care. However, a needle stick injury now carries the potential for a life-threatening transfer of infectious disease.

The great majority of hypodermic and intravenous needles are intended for a single use on an individual patient and are manufactured in a variety of designs, lengths, and gauges. Most simple needles are discarded after a single use into a biohazard collection container that contains the used needle and may also break the needle to prevent re-use. Despite all the obvious dangers associated with the use of hypodermic and intravenous needles, and the availability of many safety needle devices, unguarded needles are still routinely and predominately used in the marketplace. Due to cost considerations, many medical institutions continue to purchase unsafe needle devices.

One problem with many safety needle devices is that they are expensive and difficult to manufacture because of the intricacy of the design and the use of multiple components as part of the safety mechanism. Even when used, the incidence of failure is well known with many existing needle safety devices. Another problem associated with some of the present devices is that the protective device itself can injure the healthcare practitioner. When a protective device is difficult or clumsy to use, the action required to use the device can actually cause injury. As would be expected, the greater the number of active manipulations that must be made by hand with any safety apparatus containing a needle, the greater the risk of contact with the point. When the mechanism of use is awkward or uncomfortable, the risks naturally increase.

Moreover, any time that a safety device adds cost to a system, the added marginal cost will cause the safety device to be abandoned, or used less frequently, in a finite number of cases. Thus, simplicity and low cost are primary concerns when providing any safety device for use with an existing system. To enhance simplicity and reduce the costs of any safety system, important design criteria impact both the manufacturing process for producing the device and the operational use parameters of the device in everyday practice. Furthermore, the ideal safety device offers universal design that may be used with a large number of common devices, while also being able to be specifically designed and configured to cooperate with the underlying systems for which the safety margin is provided.

Therefore, the dangers inherent in the use of hypodermic and intravenous needles would be reduced by a safety device that has a low cost of manufacture, a simplicity of use, and that provides an effective needle protection apparatus with universal application.

SUMMARY OF THE INVENTION

The present invention is a needle point protector device and assembly for hypodermic and intravenous needles, catheters, introducers, and similar devices. The invention includes a needle cannula guide and needle point guard built into an integrated device such that the motion of the needle cannula, exerted by a single sliding motion of an integrated handle after needle use, causes the cannula and the point of the needle to pass within a needle guide and causes the needle point to engage the needle point guard in a manner that permanently fixes the needle cannula and needle point in a position and orientation that provides safety to the user. The needle point engages the needle guard when the handle of the protector, which is fixed to the needle cannula, is moved to retract the length of the needle cannula along a needle guide to a fully retracted position defined by a position where the needle point is proximal of, and no longer supported by, the needle guide. At this point, an existing tension exerted on the needle cannula causes the needle cannula and point to depart from the position within the needle guide and to spring into place proximate to or in engagement with the needle point guard. The needle point guard is proximate to the needle guide and oriented in the direction towards which the tip is biased by the tension, typically downward or in the direction of the needle guard.

In a preferred embodiment, the needle protector handle slides along a path defined by an elongate element that is integrated with and attached to the needle point guard and needle cannula guide. The elongate element traverses the handle through a channel or is attached thereto with other connector such that the protector handle slidably engages the element along a defined length thereof. Preferably, the body or housing of the handle is traversed by the elongate element to slide along a range of motion that includes an open position where the needle cannula is supported by the guide and wherein the needle point extends distally of the guide, the guard, and the elongate element. This open position is the ordinary configuration in which the needle is used to penetrate the skin of a patient. A closed position is defined by manipulating the device into a position that causes the needle point to engage the needle point guard, specifically, by moving the handle along the elongate element in a distal to proximal direction. During this motion, tension is exerted on the cannula by the orientation of the cannula in the handle body and positioning of the cannula within the needle guide until the point clears the needle guide and the tension is released causing the point to move into place proximate the point guard. The motion of the handle is restricted by a stop, for example at the proximal end of the elongate element, that prevents further motion of the protector handle beyond the point at which the tension on the needle cannula is released to spring the needle point into the safety position.

For some applications, the elongate element is capable of linear expansion or "telescoping" such that the overall length of the elongate element may be less than the total distance necessary, which is essentially the distance comprised of the sum of the length of the exposed needle cannula and the length of the protector handle. In this embodiment, when the elongate element expands from a minimum length to a maximum length as the needle cannula is withdrawn to the point where the needle point departs from the needle guide and springs into position at the needle point guard. In this embodiment, in the closed or unexpanded position, the overall length of the elongate element and the introducer handle may be shorter than the length of the cannula between the distal portion of the handle and the needle guide. However, as noted above, the telescoping action of the elongate element is sufficient for the handle to be withdrawn along the path of the elongate element such that the needle moves into position at the needle guard prior to the point at which the proximal portion of the handle abuts the stop of the elongate element.

Preferably, the proximal portion of the needle cannula is entirely contained within the body or housing of the handle such that it is fixed therein. The handle of the protector is comprised of a body or housing that contains the most proximal portion of the cannula and may completely contain a chamber in fluid communication with the proximal end of the cannula of the needle. The needle protector handle or body also contains a port that is preferably located at the most proximal portion of the handle body and is also in fluid communication with the chamber. The port has a discrete closure apparatus or fixture that seals and engages the port to contain fluids that enter the chamber through the needle cannula. In a preferred embodiment, the closure may have a septum or other dedicated sampling port for retrieving fluids within the chamber without removing the closure.

In use, the motion of the needle cannula and the needle point out of the guide and into proximity with the needle tip guard is caused by the motion of the handle in combination with the tension that is exerted by designing the needle cannula to be positioned relative to the needle guide and the elongate element such that tension is exerted on the cannula. Preferably, tension is exerted on the cannula along the entire range of motion between the open and closed position, but is specifically exerted when the portion of the cannula nearest to and comprising the needle point when the point reaches the most proximal point of the path along which it slides. As noted above, the orientation of the needle cannula relative to the elongate element and the needle guide provides the tension on the cannula that springs the point into the safety position near the needle guard. The tension may be provided by positioning the horizontal axis of the needle cannula within the body of the housing in a manner that is essentially parallel to the elongate element, but is below the plane defined by the height of the needle guide. Alternatively, the needle can be fixed at a slight angle such that the proximal point of the needle cannula is embedded in the body of the handle to form a slight deflection in the needle cannula along its length toward the needle guide. In either case, because of the tension exerted on the needle cannula, the cannula contacts the guide and continues to engage the guide while the handle is withdrawn along at least a portion of the length of the elongate element. As noted above, when the needle point or tip moves proximally of the needle guide, the existing tension on the needle cannula causes the needle to move to a point proximate to or in engagement with the needle point guard.

The range of motion of the handle is defined in the most distal direction along the elongate element by contact between the handle body and a structure integral with the needle guide, such as the body of the guide itself, the shield member (described below) or a forward stop element of any mechanical expedient that prevents further distal motion of the handle. Similarly, the motion of the handle in the most proximal position is preferably defined by a step stop element that contacts the handle to arrest the motion proximally. While the point of contact at either extreme of the path of travel of the handle is conveniently made with the most distal and most proximal portion of the handle, respectively, the contact point can easily re recessed within the body and the defined axial length of the handle body (discussed below) is modified accordingly.

For ease of use, the needle point guard is integral with the needle cannula guide in a shield member adapted to be held by the hand and that is located on at least one side of the cannula guide, such that the needle protector handle can be conveniently and simultaneously grasped by the user to withdraw the needle following use with a patient. In a preferred embodiment, the shield member is integral with, and oriented generally perpendicular to, the elongate element and has a distal portion shaped to accommodate a companion device with which the protector is used.

For example, the shield member may have a planar structure on both sides of the needle guide such that either side of the shield member can be conveniently grasped when the needle cannula is inserted through the companion device, such as a catheter insertion device that is axially separated or "peeled" apart, sometimes referred to as a "T-peel." See U.S. Pat. No. 5,951,518, PCT WO 99/22804. The shield member shape that accommodates "a T-peel catheter introducer is simply one example of the design and configuration of the distal end of the needle point protector device that surrounds and contains the needle cannula guide and point guard and which facilitates the attachment or operational combination of the overall protector device with a companion device. The companion device may be the T-peel catheter introducer, or may be any different apparatus for vascular access that is used as described herein. Depending on the design of these companion devices, the distal portion of the needle point protector may be shaped for close, intimate contact and attachment at the point of the connection to the needle point protector of the invention, or may simply be shaped to accommodate easy manipulation of the distal portion of the needle point protector and the companion device. However, in a particularly preferred embodiment, the distal portion of the needle point protector is specially configured to removably attach the companion device such that the needle point guard function of the invention is provided passively through the motion of the handle achieved during withdrawal of the needle from the patient. The configuration may be provided by altering the shape of the protector itself or may be provided by an additional, reversible, locking feature.

As is explained in further detail below, the needle point protector assembly is comprised of an assembled combination of the needle point protector and a companion device, including an introducer such as a T-peel inserter or other venous/arterial access devices, or other devices that are coupled to a needle in use. The assembly comprises, or is advantageously used with, a wide variety of devices for safe access to the venous/arterial system or for needle placement or use in any environment where a needle is used on a patient and has the potential to transmit disease. Specifically, the assembly of the invention includes the needle point protector described herein in combination with companion devices such as catheters generally, other venous/arterial access devices, including, (peripherally inserted central catheters (PICC catheters), guide wires, spinal tap needles, epidural needles, intravenous fluid administration sets, short peripheral catheters, midline catheters, neonatal catheters, biopsy needles. In clinical use, the needle protector of the invention can be provided in a kit with a companion device such as the T-peel introducer, or configured as a guide wire, spinal, epidural, biopsy, or other specialty needles sold as stand-alone products.

In a particularly preferred embodiment, the needle point protector is reversibly attached to an introducer device such that the needle point protector function of the invention is essentially automatic during use. In this embodiment, withdrawal of the needle during placement of the companion device necessarily activates the needle point protector function of the invention and provides this function passively to the companion device. In this embodiment, the safety function of the device of the invention is referred to as passive because the needle protection function occurs without separate manipulation of the needle point protector relative to the insertion device, such as the T-peel inserter, because the action of removing the needle during vascular access necessarily causes the actuation of the needle point to the appropriate safety position relative to the needle point guard.

DESCRIPTION OF THE FIGURES

FIG. 1A is a side view of the needle point protector apparatus of the invention showing the introducer handle in the most distal or "open" position. FIG. 1B is a frontal view showing the orientation of the needle cannula in the needle guide in the open position.

FIG. 2 is the needle point protector showing the introducer handle withdrawn proximally relative to the view in FIG. 1 such that the needle cannula continues to engage the needle cannula guide as the handle slides along the axial length of the elongate member of the needle point protector.

FIG. 3A is the needle point protector with the handle retracted to the point where the distance from the most distal portion of the handle to the needle guide exceeds the length of the exposed needle cannula such that the tension on the needle cannula has caused the needle point to spring into place behind the needle tip guard in the "closed" position. FIG. 3B is a frontal view of the embodiment of FIG. 3A also shown in the "closed" position.

FIG. 4A is the needle point protector together with a peelable inserter such that the wings of the inserter abut the shield member of the needle point protector device and are oriented to be grasped simultaneously by the hand. FIG. 4B is a front view of the embodiment of FIG. 4A.

FIGS. 6A and 6B are the embodiments of FIGS. 3 and 5, respectively, with a locking harness that reversibly attaches a companion device to the needle point protector device and that functionally automates the operation of the needle protector. FIG. 6C is a frontal view of the embodiment of FIG. 6B.

FIG. 9A is an embodiment of the invention in the open position wherein the companion device is removably affixed to the needle point protector apparatus to yield an integrated assembly such that the movement of the needle handle alone during insertion of a vascular access device yields the needle. FIG. 9B is a top view of the embodiment of FIG. 9A. FIG. 9C is a frontal view of the embodiment of FIG. 9A.

DETAILED DESCRIPTION OF THE INVENTION

Figure 5A:
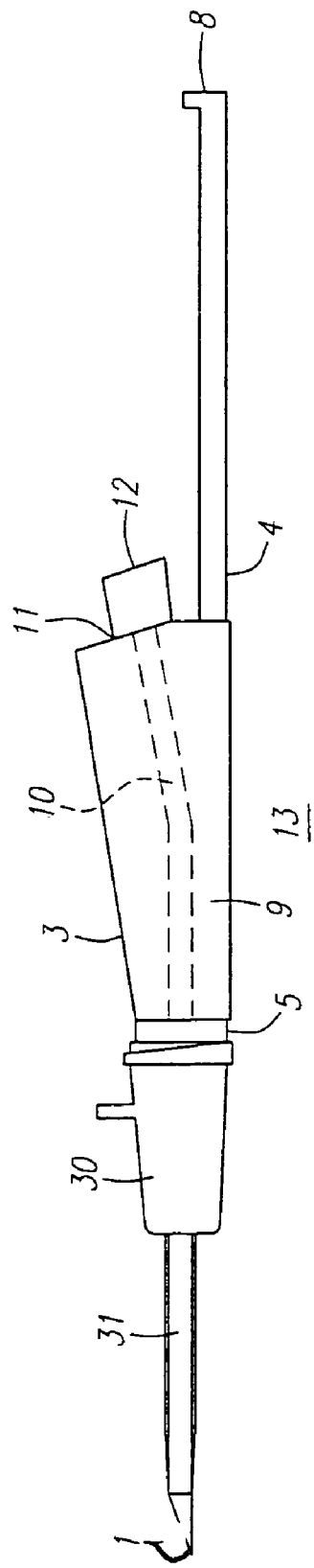
FIG. 5A is the needle point protector of the invention engaged with a conventional over-the-needle (OTN) catheter and constructed to have a male luer taper fixture attached to the distal end of the needle point protector.

Referring to FIGS. 1A and 1B, a needle for penetrating the skin and, for example, providing access to the venous or arterial system has a point 1 at the distal most end and a cannula 2 which contains a bore (not shown) through the entire length thereof for fluid communication through the needle cannula 2. The proximal end of the cannula 2 terminates in a needle protector handle 3. A proximal portion of the cannula is contained within the handle 3 and a length thereof is preferably over-molded within the body or housing of the handle 3 such that the needle cannula 2 traverses less than half of the overall axial length of the handle 3 and terminates in a flashback chamber 10 that is contained within the body of the handle 3 and is in fluid communication with the cannula 2. The chamber 10 features a sampling port 11 at the proximal end that is preferably molded directly into the body of the handle 3. The sampling port 11 has a closure 12 that sealingly engages the port 11 to prevent fluids contained in the flashback chamber 10 from leaking. In a preferred embodiment, the closure 12 has an integrated septum (not shown) or other sampling port so that fluids contained within the chamber 10 can be accessed for testing or other clinical purposes.

In this configuration, the fluid pathway begins at the needle point 1, passes through the cannula 2, continues through the portion of the cannula that traverses the handle 3, enters into the chamber 10, and may be accessed through and is controlled and contained by the closure 12 in port 11. In use, the placement of the needle point 1 in a vein or artery is accomplished with the device of the invention in the "open" configuration wherein the needle extends distally to its maximum length. Verification of proper placement of the needle point in a vein, artery, or other fluid containing body cavity is verified by the appearance of fluid in the chamber 10. Typically, the needle point protector device 13 of the invention is combined with a companion device that is intended to be placed within the body. Once the proper placement of the needle point 1 is verified, the needle can be withdrawn, as is explained in further detail below, while the companion device remains in place.

In a preferred embodiment, the body or housing of the handle 3 is conveniently grasped on both sides by the hand for ready movement of the entire needle. Reproducible movement of the needle cannula 2 is provided by engagement of the handle 3 with an elongate element 4 that has an axial length which is generally parallel with the axial length of the needle cannula 2. In this context, "axial length" refers to the long length of the needle cannula 2 through which the bore passes and, accordingly, the long length of the elongate element 4 about which the handle 3 slides. Reproducible linear movement of the needle and handle relative to the overall needle protector device is provided by a channel 9 in the body of the handle 3 through which the elongate element 4 passes and about which the handle 3 slides along the length of the elongate element 4. Thus, the elongate element 4 traverses at least a portion of the body of the handle 3 such that the handle 3 slides along a predetermined length of the elongate element 4 and, by virtue of its length and structures located at either end that define the range of motion, essentially defines the path along which the handle 3 passes. In turn, this range of motion defines the movement of the needle cannula 2 and point 1 between what is described as the open and closed positions.

To define the range of motion, the most proximal portion of the elongate element is comprised of a stop 8 or other mechanical means that limits the rearward or proximal motion of the handle 3 and which prevents the handle 3 from becoming detached from the elongate element 4 and the overall protector device 3. A mechanical stop 8 is a preferred structural element for limiting the motion proximally of the handle 3, but any structure, such as a taper in the elongate element 4 or other structural expedient can readily serve the identical mechanical purpose. At the distal end of the device 13, the range of motion of the handle 3 is limited by the shield number 5.

Referring to FIG. 1B, the distal most portion of the elongate element is integrally formed with a shield member 5 that is further comprised of the needle cannula guide 6 and the needle point guard 7. In use, the needle cannula 2 slides along its length within the guide 6 as the handle 3 is moved along the elongate element 4. The needle guide 6 may take any shape that serves to confine the needle cannula 2 in a stable, confined orientation and which contains the needle cannula 2 throughout the entire range of motion of the handle 3. As illustrated in FIG. 1B, a simple form for the needle guide 6 is a V-shaped recess in the body of the shield member 5 such that the bottom or apex of the V is aligned with the length of the elongate element 4 and the axial portion of the cannula 2. The shield member 5 is also preferably comprised of the needle point guard 7 (not shown) positioned immediately below the guide 6 but integral in the same structure of the shield member 5. The needle point guard 7 may have a lip or other concave depression in the surface of the proximal side of the shield member 5 (i.e. facing the handle 3) such that when the needle point 1 drops below the apex of the guide 6, the needle point 1 is fixed in place and prevented from moving upward and back into position above the bottom of the guide 6 such that the needle point 1 could advance distally. As is apparent from FIG. 3, when the needle point 1 drops below the needle guide 6 the point of the needle is fixed in the safety position such that the point of the needle cannot injure the user and cannot be moved in any direction, particularly axially along the length of the elongate member 4. The shield member 5 may also have a short extension (not shown) that extends distally and rests underneath a peelable inserter or other companion device (see FIGS. 2-10) to prevent rotation or movement of the companion device relative to the protector device.

As will be apparent from the description and figures herein, the needle point protector device 13 is preferably comprised of the needle, the elongate element 4 having a stop means 8, the shield member 5, together with the needle guide 6 and needle point guard 7 structures integrated therein, and the handle 3 integrated together and constructed with specific dimensions to facilitate operative function for the open and closed positions of the device. Also, the overall shape, dimensions, and configurations of the device are designed specifically to function with the catheter, introducer, or other device with which the needle point protector 13 device of the invention is used. As will also be apparent from the following drawings and description, the distal most portion of the needle point protector 13, specifically, a structure that is integral with or extends distally from the shield member 5 and which is directly abutted by the handle 3 in the open position is most specifically designed and shaped to match the design and shape of a companion device. In the embodiment of FIGS. 1A and 1B, the shield member 5, as the distal most structure of the needle point protector device 13, is advantageously shaped to facilitate use with a T-peel introducer. Accordingly, as is apparent from FIG. 1B, the shield member 5 of this embodiment has a similar size and profile to the wings of a T-peel introducer such that both may be easily grasped by the hand when the needle is used to introduce the T-peel through the skin of a patient, i.e. to access the venous or arterial system of the patient. As is seen in the figures and descriptions below, where other companion devices are used as part of a complete assembly, the distal most portion of the needle point protector device 13 will have a different shape and profile to accommodate the most proximal portion of the companion device which mates with the distal most portion of the needle point protector device 13.

Referring to FIG. 2, the embodiment of FIGS. 1A and 1B, and FIGS. 3A and 3B, is shown at an intermediate point in the operation of the device between the open configuration (FIGS. 1A and 1B) and the closed configuration (FIGS. 3A and 3B) such that the length of the needle cannula 2 is engaged by the needle guide 6 at roughly a midpoint along the length of the needle cannula 2 during the process of withdrawing the handle 3 rearward or proximally along the axial length of the elongate element 4. As the handle 3 moves along the elongate element 4, tension is exerted along the needle cannula 2 to bias the motion of the needle cannula 2 to continually engage the needle point guide 6 until the proximal point in the range of motion of the handle at which point the device achieves the closed position as illustrated in FIGS. 3A and 3B.

Referring now specifically to FIGS. 3A and 3B, the needle point protector 13 is shown fixed in the closed position wherein the safety function of the apparatus is provided by the position of the needle point 1 below the needle guide 6 and in close engagement, or actual contact, with the needle point guard 7 such that an accidental needle stick injury is prevented. Also, in this specific configuration, the most proximal portion of the handle 3 preferably engages the stop means 8 at the most proximal end of the elongate element 4. Referring to FIG. 3A, the maximum length "A" of the elongate element 4 is preferably just slightly greater than that of the length "B" of the exposed needle cannula 2, i.e. that portion of the needle cannula not contained within the housing of the handle 3, when added to the overall axial length "C" of the handle 3. Accordingly, the overall distance of the needle cannula 2 that is extended from the body of the handle 3, when added to the overall axial length of the handle 3, very closely approximates the total length of the elongate element 4 between the stop 8 and the needle point guard 7 that is integrated in the shield member 5 such that, when in the closed position, the handle 3 and needle cannula are incapable of movement in either direction along the elongate element 4 and the needle point 1 remains in close contact with the needle point guard 7. It is important that the length of the elongate element 4 closely approximates the combined lengths of the exposed portion of the needle cannula 2 and the axial length of the body at handle 3 (Length A=Length B+Length C in FIG. 3A) so that a portion of the finger or hand of a healthcare worker cannot fit between the needle point 1 and the needle point guard 7 when the needle is withdrawn to place the device in the closed position. As described above, the "axial length" of the handle 3 refers to the length of the handle 3 along the axis defined by the length of the elongate element 4 and the needle cannula 1.

As noted above, a tension is exerted on the needle cannula 2 by the orientation of the cannula 2 within the handle 3 and the position relative to the needle guide 6. As demonstrated in comparison of FIGS. 1A, 1B, 2, 3A, and 3B, the tension exerted on the needle cannula 2 against the needle guide 6 results in a displacement of the needle cannula 2 and the needle point 1 in a direction dictated by the tension such that the needle point 1 is moved into the desired position relative to the needle point guard 7. Preferably, the tension springs the needle point 1 downward to engage the needle point guard 7 and then rest a portion of the cannula 2 along the elongate element 4. In this configuration, as is apparent from FIG. 3A, the movement of the needle point 1 or cannula 2 in a forward or more distal direction is completely prevented by the needle point guard 7 and the integral structure of the shield member 5.

Referring to FIGS. 4A and 4B, the needle protector device 13 is shown attached to a peelable introducer 20 (T-peel) wherein the wings 21 of the T-peel introducer 20 are in close engagement with the shield member 5 of the protector 13. As is apparent from FIG. 4A, when used as a companion device with the safety device 13 of the invention the T-peel has a sheath cannula 22 that runs outside a substantial length of the cannula 2, while leaving the point 1 uncovered to traverse the skin. In use, the needle protector device 13 begins in the position shown in FIGS. 4A and 4B and FIGS. 1A and 1B as the closed position, wherein the needle is advanced to the most extended position distally and wherein the handle 3 abuts the shield member 5. In the embodiment of FIGS. 4A and 4B, the T-peel introducer 20 is advantageously attached to the protector device 13 in the open position for introduction to the patient. In this embodiment, the exposed length of cannula 2 (Length B in FIG. 3A) is greater than the length of the sheath cannula 22 of the peelable introducer.

The needle is introduced transdermally to the patient thereby placing the T-peel introducer along the needle cannula 2 simultaneously with placement of the needle. When the clinician determines that the needle has been properly placed, for example by viewing fluid in flashback chamber 10, the needle may be withdrawn while leaving the T-peel introducer 20 in place. To withdraw the needle, the handle 3 is pulled rearwardly, or proximally, along the elongate element 4 until it abuts stop 8. The T-peel introducer 20 remains in place to facilitate its ordinary function, while the act of withdrawing the handle 3 causes the needle to retract into the safety position and to engage the needle point guard 7 as described previously.

Figure 5B:
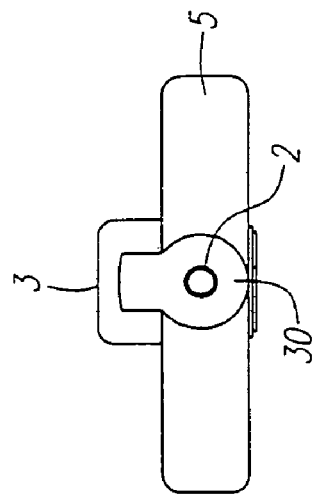
FIG. 5B is a frontal view of the embodiment of FIG. 5A with the OTN catheter engaging the needle point device.

Referring to FIGS. 5A and 5B, the needle point protector 13 is shown coupled with an over-the-needle (OTN) catheter 30 such that the most proximal portion of the catheter 30 directly contacts and abuts the distal portion shield member 5 of the needle point protector 13. As noted above, the distal most portion of the protector 13 is configured according to the shape of the proximal portion of the companion device with which the protector 13 is used to preferably yield a sealed connection. In this embodiment, the distal most portion of the protector 13 is configured to feature a fixture (not shown), such as a male luer taper that conformingly engages the companion device, in this embodiment, the proximal portion of the over-the-needle catheter 30. In use, the needle is introduced in the manner described in connection with FIGS. 4A and 4B, namely, the needle is introduced transdermally i.e. to the vascular system of a patient in a conventional fashion, while simultaneously introducing the catheter 30 and the integrated catheter cannula 31 that surrounds the needle cannula 2 when the companion device is attached to the needle point protector 13. Once proper placement of the catheter 30 is achieved, the needle is removed by actuating handle 3 to move the needle point protector device 13 into the closed position, leaving the catheter 30 in the desired placement while providing a margin of safety from a needle point injury when the needle is withdrawn.

Thus, as is apparent from FIGS. 5A and 5B, the use of the introducer 13 introduces the combination of the needle point 1, the needle cannula 2, and the proximal portion of the shaft 31 of the over-the-needle catheter 30 through the skin of the patient, for example to provide venous or arterial access. As described above, the handle 3 is withdrawn by a proximal motion along the length of the elongate element 4 such that the cannula 2 and the point 1 are positioned to the point at which the tension on cannula 2 displaces the needle point 1 out of the needle guide 6 and into engagement with the needle point guard 7, preferably when the handle reaches the most proximal position along the elongate element 4 and is abutting the stop 8. At this point, access to the venous/arterial system can be provided by accessing the port 11, the selectable access port in fixture 12, or by removing the protector 13 entirely leaving only the over-the-needle catheter in place. An analogous methodology is followed for any of the devices with which the protector 13 is used such as intravenous solution administration sets, biopsy needles, guide wires, and other similar apparatus.

Referring to FIGS. 6A and 6B, an embodiment of the invention includes a separate fixture that reversibly attaches or locks the companion device to the distal most end of the protector 13. A discrete locking fixture 40 preferably extends from the distal most end of the shield member 5 of the protector device 13 and may traverse the portion of the shield member 5 comprised of the guide 6 such that when companion devices are brought into contact with the distal end of the protector 13, the locking fixture 40 is manipulated to attach the companion device in a manner that allows the needle cannula 2 to enter the complimentary shaft or cannula on a companion device and wherein the locking fixture 40 engages the proximal most portion of the companion device to hold the companion device and the protector 13 into a single functional needle point protector assembly. In this assembled configuration, the companion device and protector 13 are functionally joined so that the motion of the needle handle 3 to retract the needle into the safety position may be performed without separate manipulation of the companion device or the protector device 13.

FIGS. 6A and 6B show the locking fixture 40 attached to the proximal most portion of an over-the-needle catheter introducer 30. In a preferred embodiment, the locking fixture 40 is a simple wire that is affixed to the shield member 5 on both sides of the needle cannula 2 and needle guide 6 to essentially straddle the cannula 2 and the proximal portion of the companion device. Ideally, the locking fixture 40 is configured to engage a structure on the companion device that provides for conforming engagement between the protector 13 and the companion device when the locking fixture 40 is actuated. In use, the protector 13, in the open position, is brought into attachment with the companion device. Then, the locking fixture 40 is positioned to engage the proximal portion of the companion device in an orientation to hold the companion device in contact with the distal most portion of the protector 13. The combined assembly is then used in the manner dictated by the clinical circumstances, followed by retraction of the needle by motion of handle 3 into the closed position. When indicated, the entire protector 13 is then removed from the companion device by reversing the attachment of the locking fixture 40 to disconnect the protector 13 from the companion device.

Figure 7A:
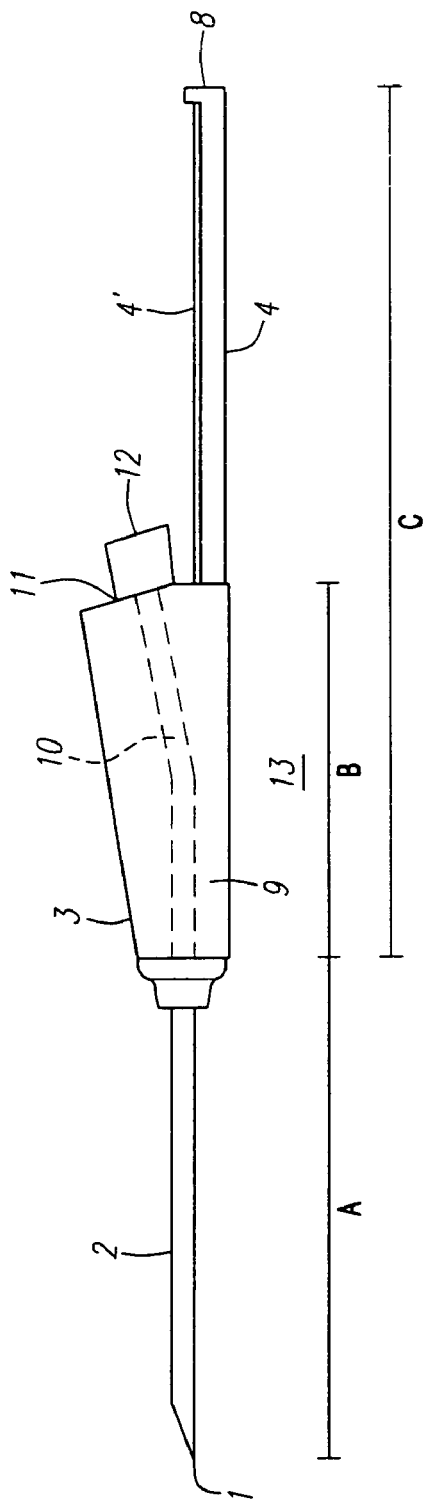
FIG. 7A is the needle point protector with a fixture at the distal end that is adapted to receive a guide wire or other assembly and with a telescoping elongate element capability and shown in the open position.
Figure 7B:
FIG. 7B is a frontal view of the embodiment of FIG. 7A.
Figure 7C:
FIG. 7C is a rear view of the embodiment of FIG. 7A.
Figure 8A:
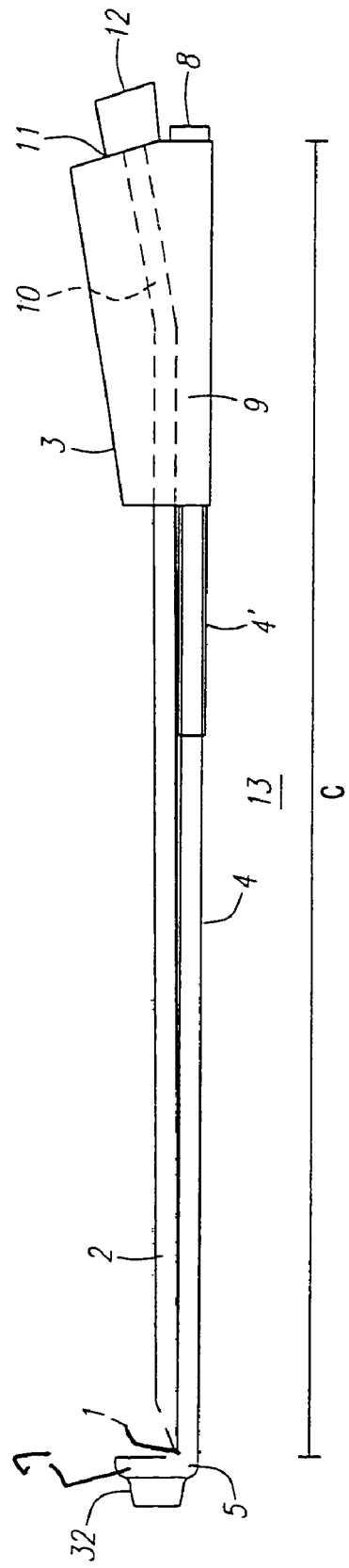
FIG. 8A is the needle point protector with a telescoping elongate element generally used to accommodate longer needle cannulas and shown in the closed position.
Figure 8B:
FIG. 8B is a frontal view of the embodiment of FIG. 8A.
Figure 8C:
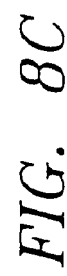
FIG. 8C is a rear view of the embodiment of FIG. 8A.

Referring to FIGS. 7A-7C, an embodiment of the invention is shown wherein the distal most portion of the protector 13 has connector 32 suitable for engaging an introducer for an apparatus such as a guide wire and which features a needle cannula 2' of extended length. Certain clinical applications require that long-straight needles be used for venous or arterial access and the protector 13 design of the invention can accommodate any needle cannula 2' length by altering the design of the elongate element 4 accordingly. Most simply, the elongate element 4 can simply be lengthened to a measurement, consistent with the embodiment described above in FIG. 3A, such that the total length "A" of the exposed cannula 2 plus the axial length of the handle 3B is substantially identical to the elongate element 4. An extended length of the elongate element 4 can also be provided with a simple extension or telescoping capability. The telescoping extension capability requires a separate movable elongate element 4' that slidingly engages the elongate element 4 and wherein the two structures move substantially coaxially with one another. Preferably, either the elongate element 4, or the movable elongate element 4' that extends the greatest distance proximally from the needle cannula 2 also contains the stop means 8 to arrest the motion of the handle 3 once the needle point is in position proximate to needle point guard 7. FIGS. 8A-8C show the embodiment of FIGS. 7A-7C wherein the elongate element 4 and movable elongate element 4' are positioned at a maximum extendable length "C" to accommodate the long needle cannula 2' and wherein the handle 3 is at the most proximal position abutting stop 8 to place the needle protector device 13 in the closed position.

As indicated above, an embodiment of the invention provides an essentially passive function for the safety needle point protection aspect by removably attaching the companion device to the distal most portion of the protector 13 using a fixture on the device 13. As is illustrated in FIGS. 9A-9C, the shield member 5 is configured to have an extension comprised of an attachment means 50 to engage the companion device in such a manner that the two devices are joined into a single assembled unit for use. As is specifically shown in FIG. 9B (wherein the handle 3 is not shown), the attachment means 50 is specifically configured to engage a companion device by contacting the device in close engagement about at least a portion of the periphery thereof and is configured to resist force applied to the protector 13, e.g. by pulling on handle 3. In the embodiment of FIGS. 9A-9C, the shield member 5 is comprised of the attachment means 50 that engages the outer edges of the wings 21 of the T-peel 20 by providing the shield member 5 with a shaped extension that acts to reversibly connect the T-peel 20 to the shield member extension. The attachment means 50 also prevents inadvertent detachment from the protector 13. As noted above, this embodiment is termed a passive device because the needle protective function is essentially added to the companion device, whether it be the T-peel introducer 20 of FIGS. 4A-4C and 9A-9C, a catheter of FIGS. 5A-5C, or any other apparatus used with the device 13, without separate manipulation thereof such that the needle protective function is provided to the entire assembly through only the motion of the handle 3.

Figure 10A:
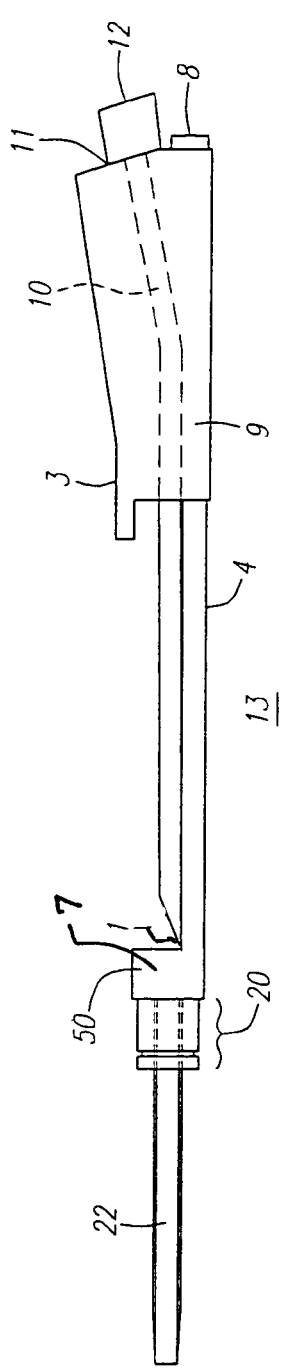
FIG. 10A is a passive embodiment of the needle protector of the invention in the closed position such that the T-peel inserter, as an exemplary companion device, is removably attached to the distal portion of the protector such that the simple act of withdrawing the needle from the T-peel inserter leaves the protector attached to the companion device but operatively retracts the needle cannula until the point is brought into engagement with the needle point guard to complete the needle point safety function of the invention.
Figure 10B:
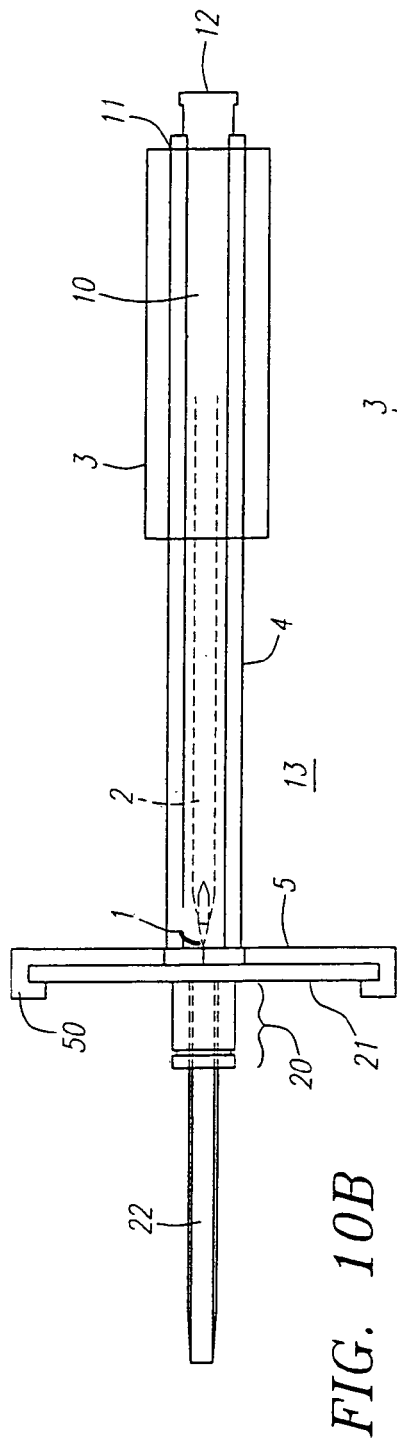
FIG. 10B is a top view of the embodiment of FIG. 10A.
Figure 10C:
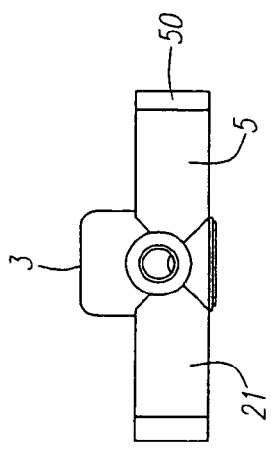
FIG. 10C is a frontal view of the embodiment of FIG. 10A.

FIGS. 10A-10C show the passive aspect of the embodiment of FIGS. 9A-9C wherein the needle point 1 has been retracted to engage the needle point guard 7 with the T-peel introducer 20 remaining attached to the attachment means 50 integrated with the distal most portion of the protector 13.

As is apparent from the above description, the precise techniques for using the device of the invention will vary with the companion device to which the needle protector device 13 is joined to form the integrated assembly. Generally, the companion device is engaged with the distal end of the protector device and positioned such that the needle point 1 extends through the companion device to be positioned for transdermal insertion into a patient. The entire assembly is inserted transdermally to a position in side the patient dictated by the clinical circumstances. Once the position is correct, the handle 3 of the device 13 is withdrawn as described previously thereby changing the configuration of the device from the open to the closed position. At that point, the needle point is in the safety position and the device 13 is still engaged with the companion device. At this point, the entire device 13 is removed leaving the companion device in place. Next, the companion device is used in the desired manner, i.e. for the introduction of a catheter, guide wire, separate needle, or other device indicated by the clinical circumstances. In a commercially preferred embodiment of the invention, the needle protector device 13 is packaged together with a companion device for insertion of a catheter, biopsy needle, PICC catheter, or similar device in a prepackaged kit where the components have been sterilized and prepared for use with a patient and including instructions for use of the needle protector device 13 and any companion device.

There will be various modifications, improvements, and applications of the disclosed invention that will be apparent to those of skill in the art, and the present application encompasses such embodiments to the extent allowed by law. Although the present invention has been described in the context of certain preferred embodiments, the full scope of the invention is not so limited, but is in accord with the scope of the following claims. All references, patents, or other publications are specifically incorporated by reference herein.

What is claimed:

1. A needle safety device comprising:
   a needle having a tip and a cannula, wherein the needle cannula is in fluid communication with a chamber disposed inside a body of a housing comprising a handle, and wherein a proximal portion of the needle is fixed in a distal portion of the housing such that the body of the housing anchors the needle cannula extending into the body of the housing, and wherein the proximal portion of the needle cannula is deflected at an angle to exert tension on the needle cannula against a needle guide;

an axial elongate element traversing the housing and having an integral needle point guard at a distal end thereof for arresting motion of the needle tip distal of the needle guide, wherein the needle cannula extends from the housing and is exposed along the length thereof such that the exposed length of the needle cannula and the housing are slidable along a length of the axial elongate element;

a shield member having the needle guide disposed therein wherein movement of the housing causes the exposed needle cannula to engage the needle guide along the length of the exposed needle cannula; and means for arresting the movement of the handle located at a proximal end of the elongate element.

2. The safety device of claim 1 wherein the exposed length of the needle cannula is not contained within the body of the handle housing or the needle guide and wherein the housing is slidable along the axial elongate member.

3. The safety device of claim 2 wherein release of the tension moves the needle tip out of the needle guide into proximity with the adjacent needle point guard.

4. The safety device of claim 2 wherein the shield member is integral to a distal end of the axial elongate element.

5. The safety device of claim 4 wherein the shield member is shaped to conform to a companion device.

6. The safety device of claim 5 wherein the conforming shape is an extension that reversibly attaches the companion device.

7. The needle safety device of claim 1 wherein the proximal portion of the axial needle cannula fixed in the body of the housing and deflected at an angle relative to the elongate element is over-molded in the body of the housing.

8. A needle safety device comprising:

a needle having a point and an exposed axial needle cannula having a proximal portion fixed in a housing comprising a handle wherein the proximal portion of the axial needle cannula is deflected at an angle to an elongate element that engages the body of the housing, and wherein the housing is slidable along a path defined by the axis of the elongate element such that, as the housing slides along the elongate element, contact is maintained between the exposed axial needle cannula and a needle guide located at a distal end of the axis at the elongate element, and wherein the safety device moves between two positions comprising:

an open position wherein the needle point extends distally of the needle guide and the handle is in a distal position along the axial path defined by the elongate element, and a closed position wherein the housing is positioned proximally to a point that positions the needle point proximal of the needle guide and proximate to a needle point guard.

9. The safety device of claim 8 wherein contact between the needle point and the needle point guard when the device is in the closed position prevents motion of the housing distally.

10. The safety device of claim 8 wherein a transition from the open to the closed position is achieved by moving the housing from a most distal position at the axis of the elongate element to a most proximal position of the axis of the elongate element.

11. The safety device of claim 10 wherein the most distal position is created by contact between the housing and the shield member and the most proximal position is created by contact between the housing and a stop means integral with the axial elongate element.

\* \* \* \* \*